United States Patent [19]

Stack et al.

[11] Patent Number: 5,527,337
[45] Date of Patent: Jun. 18, 1996

[54] BIOABSORBABLE STENT AND METHOD OF MAKING THE SAME

[75] Inventors: Richard S. Stack, Chapel Hill; Howard G. Clark, Durham, both of N.C.; William F. Walker, Holcomb, N.Y.; James H. McElhaney, Durham, N.C.

[73] Assignee: Duke University, Durham, N.C.

[21] Appl. No.: 200,556

[22] Filed: Feb. 22, 1994

Related U.S. Application Data

[63] Continuation of Ser. No. 701,154, May 17, 1991, abandoned, which is a continuation-in-part of Ser. No. 658,708, Feb. 21, 1991, abandoned, which is a continuation-in-part of Ser. No. 524,884, May 18, 1990, abandoned, which is a continuation-in-part of Ser. No. 66,345, Jun. 25, 1987, Pat. No. 5,059,211, said Ser. No. 701,154, is a continuation-in-part of Ser. No. 649,534, Feb. 1, 1991, Pat. No. 5,306,286, which is a continuation of Ser. No. 66,345.

[51] Int. Cl.$^6$ .................................................. A61M 29/00
[52] U.S. Cl. ............................................ 606/198; 623/901
[58] Field of Search ..................................... 606/108, 198, 606/191, 151, 153–156; 623/1, 12, 901

[56] References Cited

U.S. PATENT DOCUMENTS

| | | |
|---|---|---|
| 2,127,903 | 8/1938 | Bowen . |
| 3,657,744 | 4/1972 | Ersek . |
| 3,789,852 | 2/1974 | Kim et al. ............................ 606/198 X |
| 4,655,771 | 4/1987 | Wallsten . |
| 4,665,918 | 5/1987 | Garza et al. ............................ 623/12 X |
| 4,693,249 | 9/1987 | Schenck . |
| 4,733,665 | 3/1988 | Palmaz . |
| 4,740,207 | 4/1988 | Kreamer . |
| 5,007,926 | 4/1991 | Derbyshire . |
| 5,019,090 | 5/1991 | Pinchuk . |
| 5,037,427 | 8/1991 | Harada . |
| 5,089,006 | 2/1992 | Stiles ........................................ 606/198 |
| 5,100,429 | 3/1992 | Sinofsey et al. ........................ 606/195 |
| 5,171,262 | 12/1992 | Mac Gregor ............................ 623/12 |
| 5,344,426 | 9/1994 | Lau et al. .................................. 623/1 |

FOREIGN PATENT DOCUMENTS

| | | |
|---|---|---|
| 0246998 | 11/1987 | European Pat. Off. . |
| 0349505 | 1/1990 | European Pat. Off. . |
| 0408245 | 1/1991 | European Pat. Off. . |
| 0528039 | 2/1993 | European Pat. Off. . |
| WO90/001969 | 3/1990 | WIPO . |
| WO90/004982 | 5/1990 | WIPO . |
| WO91/012779 | 9/1991 | WIPO . |

*Primary Examiner*—Michael H. Thaler
*Attorney, Agent, or Firm*—Cushman Darby & Cushman

[57] ABSTRACT

A bioabsorbable stent for placement at the locus of a stenotic portion of a body passage, such as a blood vessel, which is flexible and compliant for safe and effective delivery to the site of the stenotic portion of, for example, a blood vessel, and so as to avoid the disadvantages of chronic implantation, such as arterial rupture or aneurism formation while exposed to the continuous stresses of a beating heart. The stent is formed from a bioabsorbable material and is porous or has apertures defined there through to facilitate tissue ingrowth and encapsulation of the stent. The stent is encapsulated and biodegrades or bioabsorbs within a period of days, weeks or months as desired following encapsulation to thereby minimize the likelihood of embolization or other risks of the dissolved material and to avoid the disadvantages of chronic implantation.

14 Claims, 7 Drawing Sheets

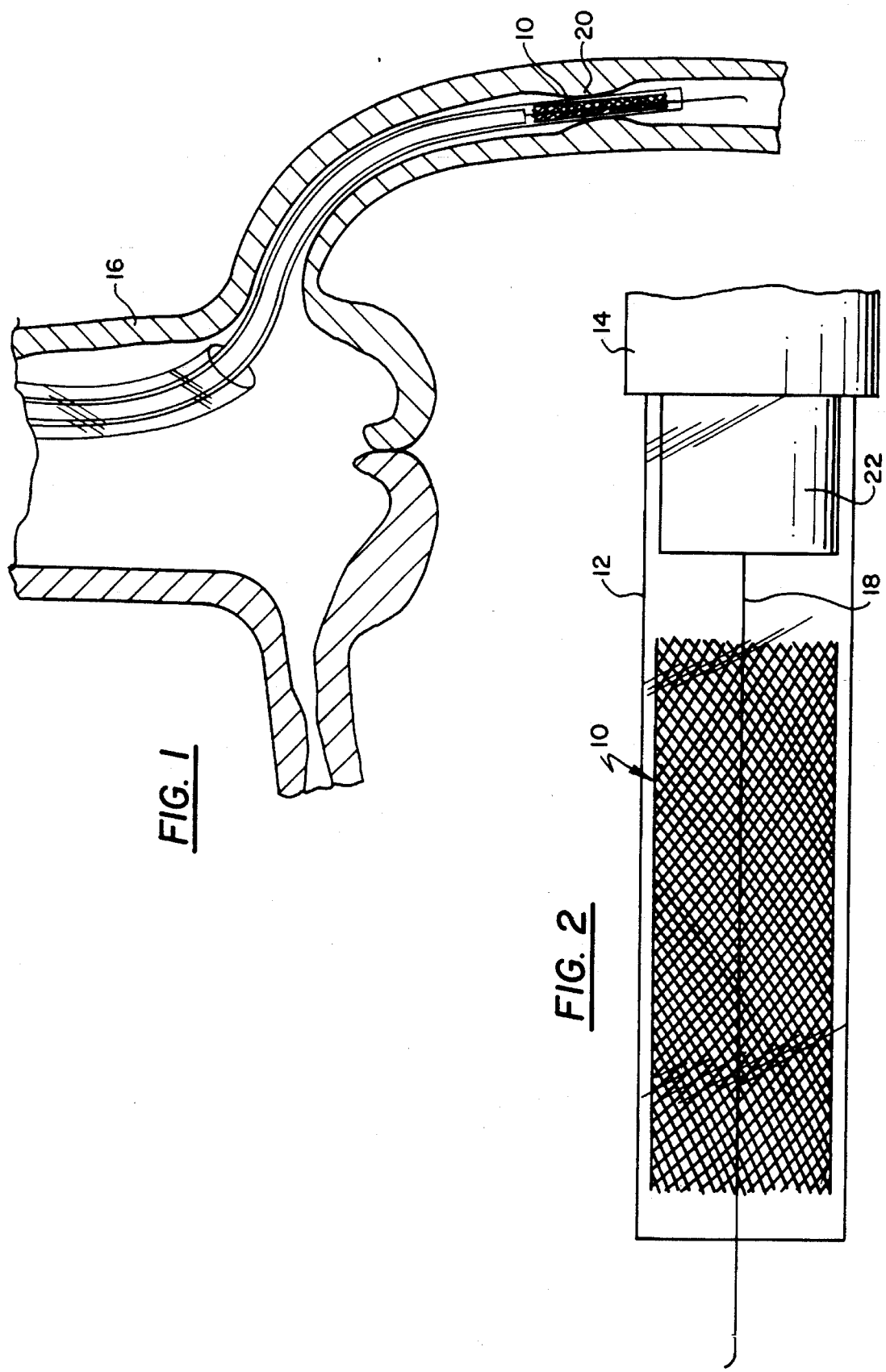

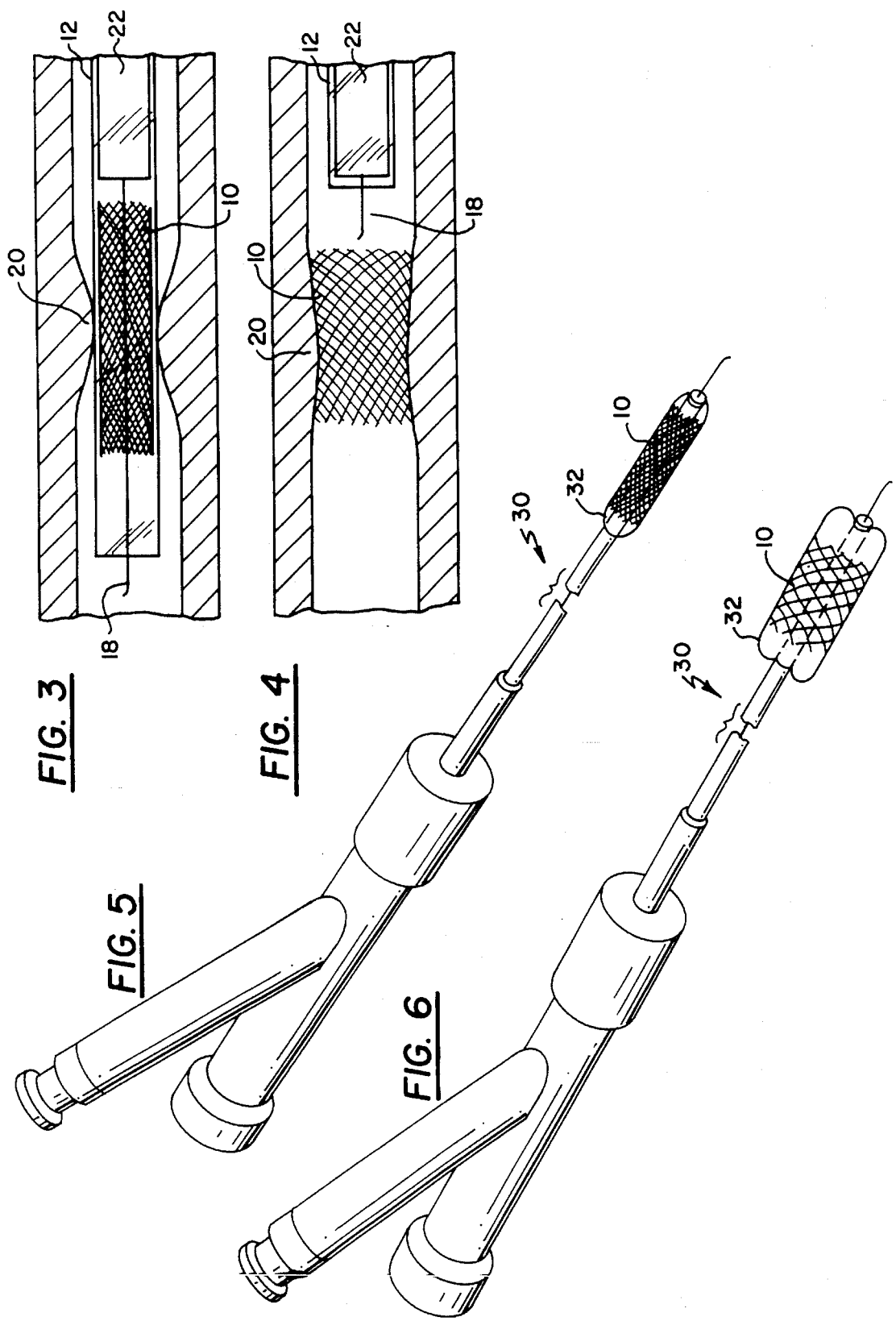

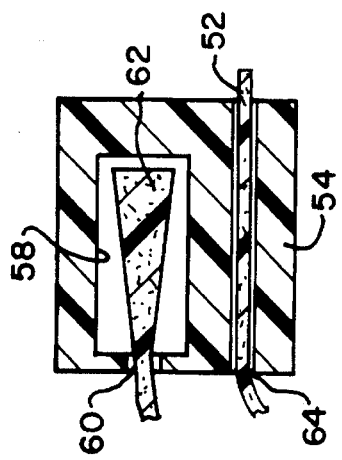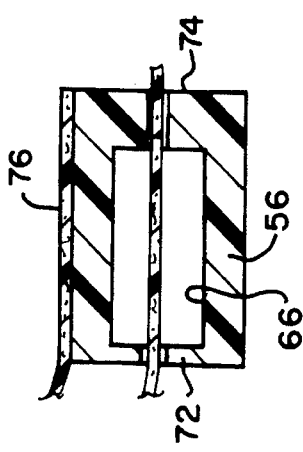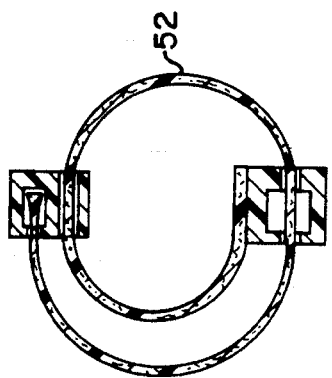

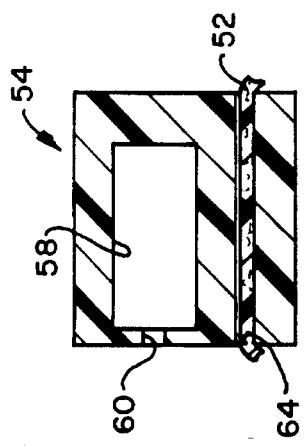
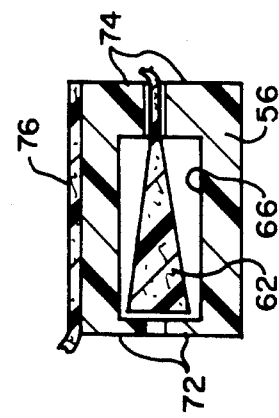
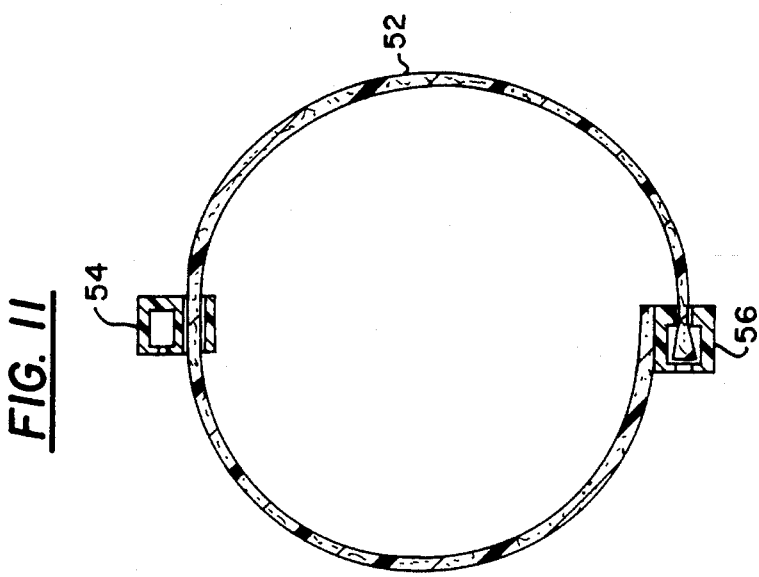

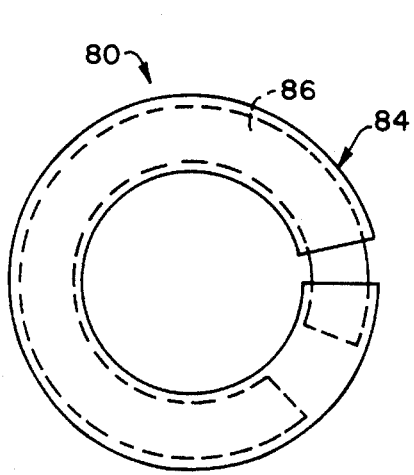
FIG. 15
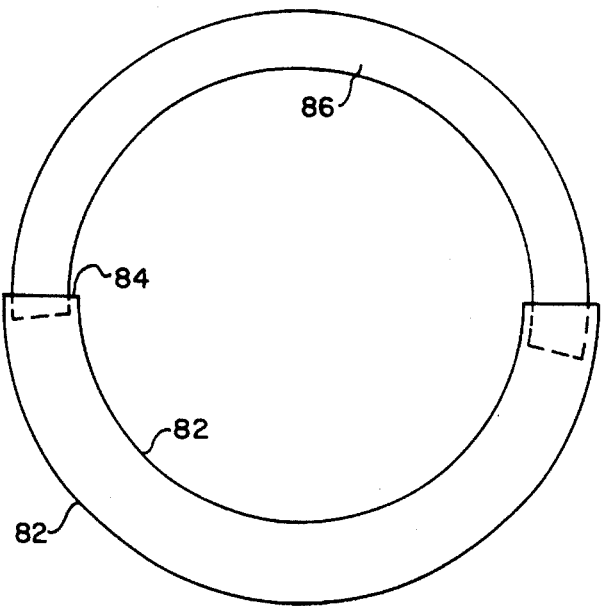
FIG. 16
FIG. 14
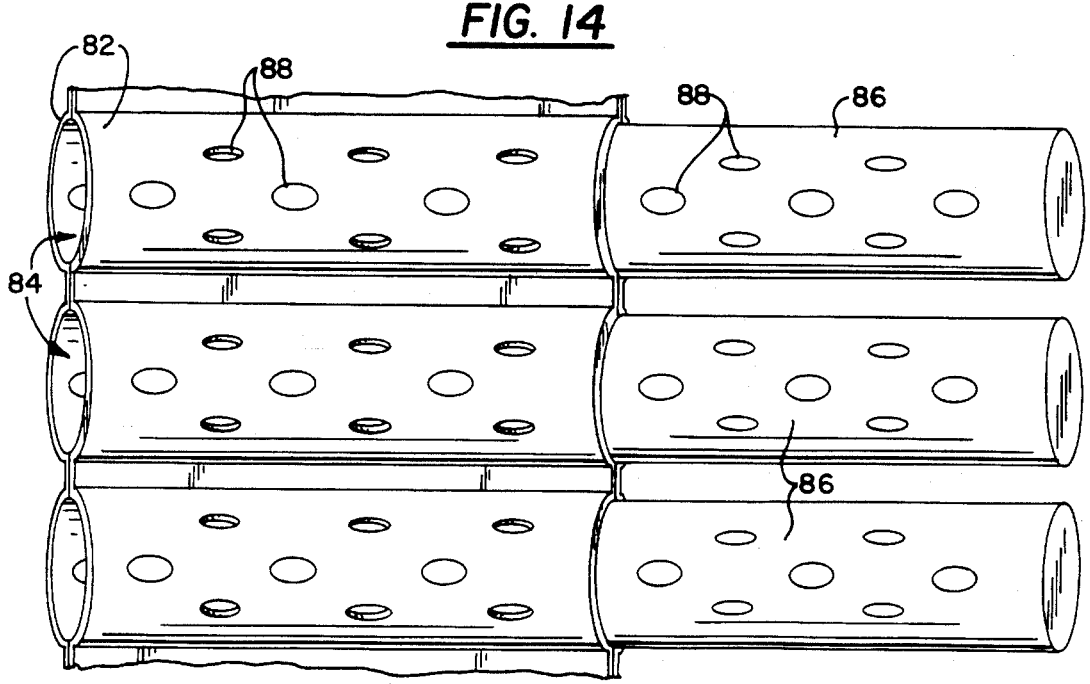

BIOABSORBABLE STENT AND METHOD OF MAKING THE SAME

The invention described herein was made in the course of work under grant or award from the U.S. Department of Health and Human Services.

This is a continuation of application Ser. No. 07/701,154, filed May 17, 1991, now abandoned, which is a continuation-in-part of application Ser. No. 07/658,708, filed Feb. 21, 1991, now abandoned, which is a continuation-in-part of application Ser. No. 07/524,884, filed May 18, 1990, now abandoned, which is in turn a continuation-in-part of application Ser. No. 07/066,345, filed Jun. 25, 1987, now U.S. Pat. No. 5,059,211. application Ser. No. 07/701,154, is also a continuation-in-part of application Ser. No. 07/649,534, filed Feb. 1, 1991, now U.S. Pat. No. 5,306,286, which is a continuation of application Ser. No. 07/066,345, now U.S. Pat. No. 5,059,211, the disclosures of all of the listed applications being incorporated herein by reference.

BACKGROUND OF THE INVENTION

1. Field of the Invention

This invention relates to a stent for maintaining the patency of a body passage. In addition to maintaining patency, the stent can serve as drug delivery vehicle to effect localized pharmacologic therapy. The invention has particular application in the field of coronary angioplasty and will be described with reference thereto. In that realization the invention primarily relates to bioabsorbable (and thus biodegradable) stents for placement within a blood vessel, such as a coronary artery, to treat acute arterial closure and to prevent restenosis following angioplasty. However, the invention may also advantageously find application in dilating and maintaining the patency of other body passages, such as the ureters and the fallopian tubes.

2. Description of the Related Art

Coronary angioplasty typically involves the use of a catheter system including a dilation catheter which is introduced via the femoral artery under local anesthesia and is advanced to the site of a stenotic lesion in a coronary artery. The dilation catheter is for example a balloon catheter which is inflated with a fluid once it has been disposed within the targeted stenotic portion of the coronary artery. As the balloon is inflated, the atherosclerotic material along the vessel walls is compressed to thereby dilate the flow passage through the coronary artery.

While balloon angioplasty has become a relatively common and successful procedure, restenosis following angioplasty frequently occurs. Furthermore, the atherosclerotic plaque can crack during expansion which greatly increases the likelihood that the coronary artery will subsequently collapse.

It would therefore be desirable to avoid or minimize restenosis of a blood vessel, such as a coronary artery, by maintaining atherosclerotic plaque in its compressed disposition while at the same time preventing vessel collapse.

With the foregoing object, metallic stents have been developed and carried to stenotic portions of coronary arteries for placement after the vessel segment has been dilated by a balloon catheter or at the time of atherosclerotic plaque compression.

One such metallic stent has been proposed and tested in Europe and described in the article of Sigwart, et al titled "Intravascular Stent to Prevent Occlusion and Restenosis after Transluminal Angioplasty", published in the *New England Journal of Medicine*, Vol. 316, 12, Mar. 19, 1987, pp. 701–706. That stent is a metallic "Chinese finger handcuff" which can be expanded in diameter while simultaneously reduced in length and compressed in diameter while simultaneously elongated. The stent remains in its distorted configuration after the distorting force is removed.

The metallic stent is made by cutting a desired length from an elongated tube of metal mesh. As a result, it has the disadvantage that metal prongs from the length cutting process remain at the longitudinal ends of the stent. The inherent rigidity of the metal used to form the stent together with the terminal prongs make navigation of the blood vessels to the locus of the targeted stenotic lesion difficult as well as risky from the stand point of injury to healthy tissue along the passage to the target vessel. Further, once the stent has been permanently disposed within the target vessel, the beating of the patient's heart can cause the terminal prongs to damage the healthy vessel walls adjacent to the stenotic portion of the artery, even after endothelial encapsulation. This damage can lead to arterial rupture or aneurysm formation. Finally, because the metallic stent is intended to be chronically implanted within the vessel, continued exposure of the stent to blood can lead to undesirable thrombus formation within the blood vessel.

SUMMARY OF THE INVENTION

It would therefore be desirable to provide a stent for disposition within a blood vessel, such as a coronary artery, that has sufficient hoop strength to support the vessel wall against collapse and yet is flexible and compliant enough for safe and effective delivery to the site of a stenotic portion of a coronary artery. It would also be desirable to provide a stent which is soft and compliant to avoid arterial rupture or aneurysm formation at the ends of the stent even when exposed to continuous stresses from the beating heart following implantation.

It would be desirable, in the alternative to form such a stent as a sheet of preferably though not necessarily bioabsorbable material which has been rolled into a substantially cylindrical configuration and which has at least one of pores therein and apertures defined therethrough so as to allow endothelial cells to grow into and over the stent so that bioabsorption or degradation will occur within the vessel wall rather in the lumen of the vessel and further to allow blood flow through the stent where, for example, the stent traverses a branch of the blood vessel.

It would even further be desirable to provide a stent which avoids the limitations of chronic implantation by being absorbed into the blood vessel wall after healing of the angioplasty site. It would further be desirable to form such a bioabsorbable stent in a mesh-like or helical array of strands of biodegradable/bioabsorbable material which will enable endothelial cells at the angioplasty site to grow into and over the stent so that biodegradation will occur within the vessel wall rather than in the lumen of the vessel which could lead to embolization of the dissolved material.

A bioabsorbable stent is provided in accordance with the present invention which can support a vessel wall following coronary angioplasty but which overcomes the deficiencies of prior art metallic stents. More particularly, the present invention relates to a bioabsorbable stent for placement at the locus of, for example, a stenotic portion of a coronary artery which is flexible and compliant for safe and effective delivery to the targeted portion of the coronary artery and so as to avoid arterial rupture or aneurysm formation while exposed to continuous stresses from the beating heart. The stent formed in accordance with the present invention can be a self-expanding stent formed from a plurality of strands of biodegradable material which can be deformed so as to have a reduced diameter which facilitates delivery of the stent to the targeted portion of a coronary artery and, once disposed at the target portion of the artery, can be allowed to expand to its preformed configuration to dilate and support that portion of the blood vessel. In the alternative, the stent formed in accordance with the present invention can be a sheet of bioabsorbable or biodegradable material which has been rolled in to a substantially cylindrical configuration which, through the memory of the material, will tend to expand in diameter when a force maintaining the same in a relatively reduced configuration is released.

The self-expanding stent provided in accordance with the present invention can be transported to a stenotic portion of an artery within a catheter which retains the same in its compact, reduced diameter configuration and then ejected from the catheter delivery system at the site of the stenotic lesion where it is allowed to return to its preformed configuration. In the alternative, the stent of the invention can be mounted to an expandable delivery device which maintains the stent in its reduced diameter configuration until deployment of the stent is desired. The forces maintaining the stent in its collapsed configuration are released to allow the stent to expand to its desired, preformed configuration. Expansion of the stent to its final configuration can be augmented and/or facilitated by, for example, inflating a balloon catheter therewithin to urge the stent into contact with the vessel walls to ensure maximal support of the blood vessel as well as prompt encapsulation of the stent structure. In that regard, where dilation of the stent is encouraged at the site of the stenotic lesion, plaque can be compressed at the time of stent placement rather than or in addition to prior dilation.

One skilled in the art will appreciate that a stent formed in accordance with the present invention can also be expandable from a reduced diameter configuration (as opposed to self-expanding). As such, the stent can be delivered to the locus of a lesion in a reduced diameter configuration on the distal end of an expandable catheter and can be expanded in vivo to its supporting diameter by expanding the expandable portion of its associated catheter. An expandable stent in accordance with the invention, may be a mesh type configuration or as detailed herein below may be advantageously in the form of a sheet of biocompatable and preferably bioabsorbable material. An expandable stent, in accordance with the invention, may also be formed from a plurality of sheets or strips of bioabsorbable material which are interconnected and wherein the means for interconnecting the strips of bioabsorbable material provide a means for retaining the stent in a reduced diameter configuration and a means for retaining the stent in its expanded or dilating configuration. The means for retaining the bioabsorbable stent in its reduced or expanded configuration, particularly where the stent is a sheet or segment of bioabsorbable material, can be merely the frictional forces between adjacent portions of the bioabsorbable sheet.

Other objects, features and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

BRIEF DESCRIPTION OF THE DRAWINGS

FIG. 1 is an elevational view illustrating the delivery of a stent provided in accordance with the present invention to the site of a stenotic lesion within a coronary artery;

FIG. 2 is an enlarged elevational view of a stent provided in accordance with the present invention disposed within a catheter delivery system of the type illustrated in FIG. 1;

FIG. 3 is an enlarged elevational view partly in cross-section showing the stent of the invention disposed within a targeted portion of a blood vessel, prior to disengagement from the delivery catheter assembly;

FIG. 4 is an enlarged elevational view similar to FIG. 3 but following disengagement from the delivery catheter assembly;

FIG. 5 is a perspective view of a stent formed in accordance with the present invention in its reduced diameter configuration mounted to the collapsed balloon of a balloon catheter;

FIG. 6 is a perspective view showing the stent of the invention following release and expansion of the stent upon expansion of the balloon catheter;

FIG. 8 is a cross-sectional view of the stent of FIG. 7 in its reduced diameter configuration;

FIG. 9 is an enlarged view of portion A of FIG. 8;

FIG. 10 is an enlarged view of portion B of FIG. 8;

FIG. 11 is a cross-sectional view of the stent of FIG. 7 in its enlarged cross-sectional configuration;

FIG. 12 is an enlarged view of portion C of FIG. 11;

FIG. 13 is an enlarged view of portion D of FIG. 11;

FIG. 14 is a schematic perspective view of a further alternate embodiment of the invention;

FIG. 15 is a schematic end view showing the embodiment of FIG. 14 in its reduced diameter rolled configuration;

FIG. 16 is a schematic end view of the stent of FIG. 14 in its enlarged configuration;

DETAILED DESCRIPTION OF THE PRESENTLY PREFERRED EXEMPLARY EMBODIMENTS

Figure 7:
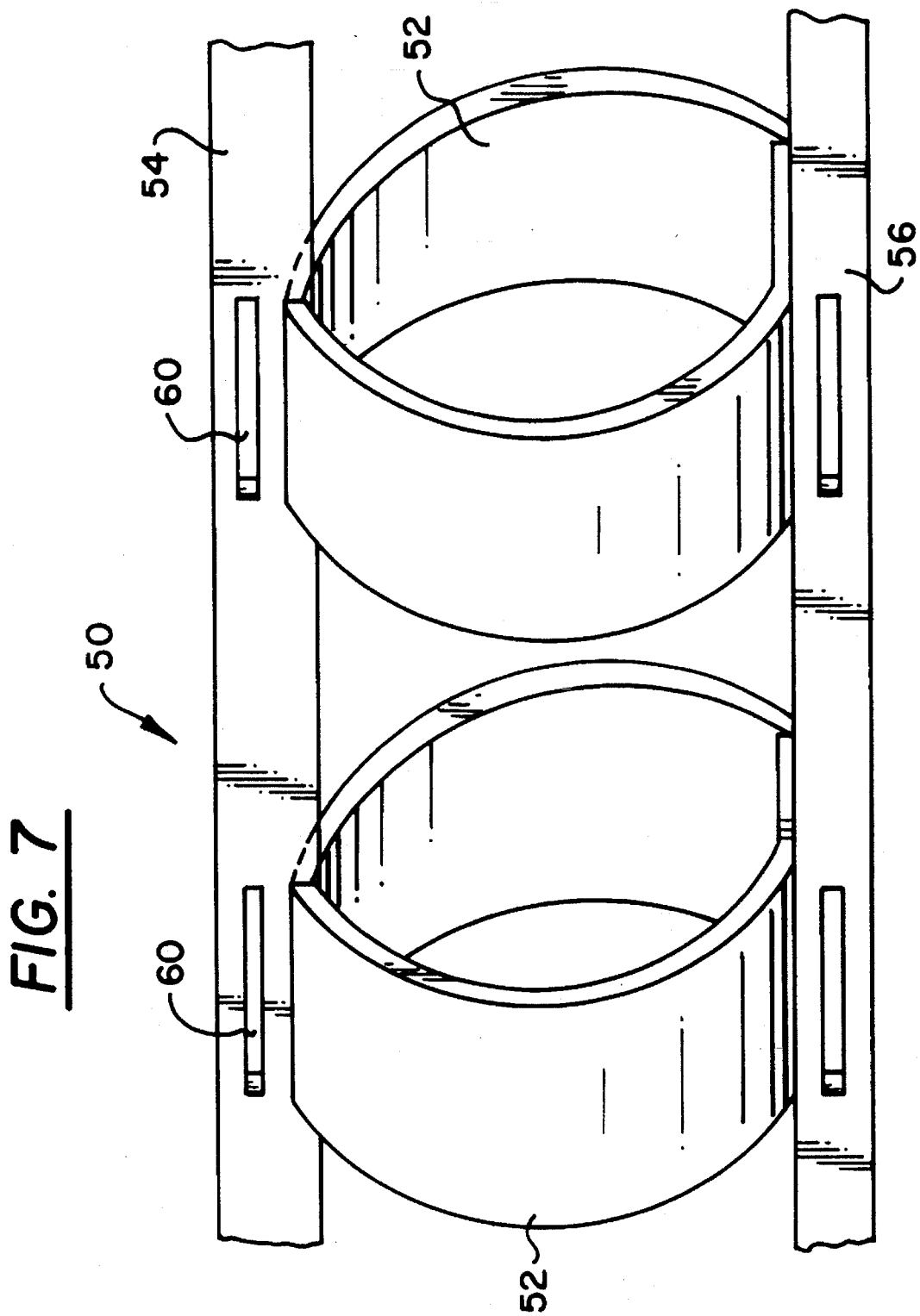
FIG. 7 is schematic perspective view showing a stent in accordance with an alternate embodiment of the invention.

The stent to which the present invention relates can be either expandable or self-expanding in form. A detailed description of a stent of the self-expanding type is provided below. The self-expanding stent provided in accordance with the present invention can be woven from a plurality of strands of biodegradable material into a diamond-braided pattern. For example, the self-expanding stent can be woven from 8 strands of a bioabsorbable polymer. Thus the strands for forming the bioabsorbable stent are extruded, drawn and then braided to form the basic tubular stent. The stent is then cut to length and heat set. The severed ends of the stent are welded together by means of laser, heat, ultrasound or glue, for example. The stent so formed has memory characteristics such that if it is distorted in length and/or diameter, it will return or tend to return to its preformed configuration upon the release of external forces. Thus the stent is self-expanding when distorted so as to reduce the diameter thereof and subsequently released. Finally, the stent is formed from a material and braided such that the stent can withstand collapse pressures in excess of 200 mmHg.

In order to deliver the bioabsorbable stent 10 of the invention to the site of a stenotic lesion, it is necessary for the external diameter of the stent to be reduced so that the stent can easily traverse the blood vessels leading to a targeted portion of a coronary artery and disposed within the reduced diameter portion of the artery. Thus, the stent must be reduced by for example elongating the stent, allowing for a corresponding reduction in diameter, and maintained in such a reduced diameter or collapsed configuration during the delivery process. Once at the targeted portion of the coronary artery, the forces tending to reduce the diameter of the stent are released whereby the stent can support and/or dilate the stenotic portion of the coronary artery.

With reference to FIGS. 1 and 2, the collapsed or reduced diameter bioabsorbable stent 10 in accordance with the present invention can be delivered to a targeted portion of a blood vessel by placing the reduced diameter stent within a delivery sheath 12 which is turn fed through a guide catheter 14 through the aorta 16 to the left or right coronary ostium. The stent carrying sheath 12 is then advanced from the distal end of the guide catheter 14 over a guide wire 18 into the targeted coronary artery and to the site of a stenotic lesion 20.

A second sheath 22 is provided proximally of the collapsed stent 10 and is used to facilitate removal of the stent 10 from the outer sheath 12. More particularly, with reference to FIGS. 3 and 4, once the sheath 12 has been disposed at the targeted stenotic portion 20 of the coronary artery, the inner, proximal sheath 22 is held in place while the outer sheath is retracted or pulled proximally with respect to the stent 10. Removal of the outer sheath 12 removes the forces which retain stent 10 in its collapsed configuration and thus allow the stent to self-expand within the stenotic portion 20 of the coronary artery to support and dilate the vessel walls (FIG. 4). The inner sheath 22 prevents stent 10 from moving proximally with outer sheath 12. The inner and outer sheaths 22, 12 as well as the guide wire 18 and guide catheter 14 can then be removed from the vascular system. In the alternative, the inner and outer sheaths can be removed and a balloon catheter (not shown in FIGS. 3 and 4) fed through the guide catheter 14 over the guide wire 18 and into the expanded stent 10. The balloon can then be inflated within the stent so as to urge the stent into firm engagement with the walls of the coronary artery and/or to augment the dilation of the artery effected by the stent alone.

With reference to FIGS. 5 and 6, in the alternative, a bioabsorbable stent 10 formed in accordance with the present invention can be delivered to the site of a stenotic portion of a coronary artery on a balloon catheter 30. More particularly, with reference to FIG. 4, the stent 10 in its reduced diameter, slightly elongated configuration can be secured to the exterior surface of a collapsed balloon 32 provided on the end of a balloon catheter 30. The stent 10 can be secured to the balloon with any suitable biocompatable glue or adhesive.

The balloon catheter 30 with stent 10 fixedly secured thereto is then fed over a guidewire 34 to the site of a stenotic portion of a blood vessel, such as a coronary artery. Once the balloon catheter 30 has been properly located, the distal balloon 32 is inflated. Inflation of the balloon 32 disengages the stent 10 from the exterior surface of the balloon by disturbing the points of adhesive securement between the stent 10 and the balloon 32. Once the adhesive securement of the stent 10 has been released, the stent is free to and tends to resume its preformed configuration and thus re-expands or self-expands. Simultaneous inflation of the balloon 32 ensures that the self-expanding stent fully expands and is in supporting engagement with the blood vessel. In addition, the dilation or inflation of the balloon can simultaneously effect or encourage the dilation of the stenotic portion of the blood vessel. Thus, the balloon catheter 30 not only provides a delivery system for the stent of the invention but ensures that the stent is fully expanded once in place and can simultaneously dilate the targeted portion of the blood vessel.

In the alternative to providing a stent in the form of a mesh, whether self expanding or positively expandable, a stent in accordance with the invention may be formed as a sheet or plurality of sheets or strips of bioabsorbable material which are formed or are rolled so as to define a substantially cylindrical configuration for expanding and supporting walls of a body passage, such as a coronary artery. Thus, in the embodiment of the invention illustrated in particular in FIG. 7, a stent 50 in accordance with the invention is in the form of a series of strips 52 of bioabsorbable material which are supported in predetermined spaced relation by first and second elongated supporting and fastening ribbons 54,56. The ribbons, like the strips are bioabsorbable.

Ribbon 54 has a compartment 58 with an access opening 60. A plurality of compartments 58 may be provided or a continuous compartment 58 with continuous or intermittent opening(s). Each strip 52 of bioabsorbable material has an enlarged longitudinal end or has a bulbous element mounted thereto so as to provide a relatively large longitudinal end 62. As shown, the bulbous end 62 of each of bioabsorbable strip 52 has tapered walls so that it gradually increases in cross-section to facilitate passage of the bulbous portion 62 through the slit or slot 60 defined in the ribbon 54, while preventing entry of the bioabsorbable strip in the reverse direction. Ribbon 54 further includes a plurality of transverse passages 64 through which each strip 52 of bioabsorbable material passes.

The second elongated ribbon 56 also defines a chamber 66 for receiving the bulbous portion 62 of the bioabsorbable strip(s) 52 and provides first and second passages 68,70 for each such receiving chamber 66. The wall thickness of ribbon 56 differs on each side of the bulbous portion receiving chamber 66. On one side, the wall has relatively thin wall portions 72 to allow deflection of the wall upon engagement of the inclined surfaces of the bulbous portion 62 of the bioabsorbable strip 52. The other wall includes relatively thick wall portions 74 which do not deflect upon engagement with the inclined walls of the bulbous portion 62 and, thus, the bulbous portion which enters through the flexible walls 72 will be retained within the chamber 66 and cannot escape from the opposite side walls 74 of the chamber 66. The opposite longitudinal end 76 of each bioabsorbable strip 52 is secured to the second ribbon 56 as shown in FIG. 10. Any suitable means can be provided for such attachment but it is envisioned that such securement can best be provided with a biocompatable glue.

Prior to insertion of the bioabsorbable stent into the body passage, the stent is in a compacted configuration as illustrated in particular in FIG. 8.

When the stent 50 illustrated in FIG. 8 is to be expanded within a desired portion of a stenotic body passage, such as a coronary artery, a force is applied from the radial center of the stent outwardly to expand the stent. This causes the bulbous portion 62 of the bioabsorbable sheets or strips 52 to be urged outwardly of the first ribbon 54 (to the left in FIG. 9) and out of the bulbous portion receiving chamber 58. At the same time, the bioabsorbable strip is fed through the passage 64 in the first ribbon 54, to the left as shown in FIG. 9. Likewise, the bioabsorbable strip moves through the bulbous receiving chamber 66 in the second ribbon 56 (to the right as illustrated in FIG. 10). Ultimately, as shown in FIG. 11, the stent will have attained its maximal diameter at which time the bulbous portion 62 of the bioabsorbable strip 52 has deflected the walls 72 of the chamber 66 in the second ribbon 56 and entered that chamber, but is incapable of further passing through the chamber 66 by virtue of the relatively thick chamber walls 74. Thus, the stent 50 illustrated in FIG. 7 is retained in its reduced diameter configuration (FIG. 8) until a force is positively applied to the stent to enlarge it to its second configuration, shown in FIG. 11. Once the stent has been expanded, the bulbous portion 62 is captured in the second ribbon 56 and cannot exit that chamber 66 either back through the deflectable walls 72 or forwardly through walls 74 of that chamber. Thus, the stent will similarly be retained in it large diameter configuration.

Because the bioabsorbable strips are spaced apart along the length of the stent, blood can flow outwardly from within the stent to without, between the adjacent bioabsorbable strips and it is unnecessary to provide apertures allowing blood flow directly through the bioabsorbable stent material. However, such apertures can be provided and may be desirable to encourage tissue ingrowth. Otherwise, the strips of bioabsorbable material may advantageously have pores therein and/or apertures to allow both blood flow and tissue ingrowth. If the strips are sufficiently small in width, that is small in the dimension extended along the length of the stent, then such pores and/or apertures may be unnecessary.

As yet a further alternative, the bioabsorbable stent 80 formed in accordance with the present invention can be in the form of a pair of sheets 82 of bioabsorbable material which have been interconnected so as to define tine receiving cavities 84 with pieces of a solid bioabsorbable material in the form of plurality of tines 86 interconnected to the tine receiving cavities. Thus, the tine elements 86 are interconnected to first ends of the tine receiving cavities 84, as shown in FIG. 14, and the bioabsorbable structure can be rolled into a substantially cylindrical configuration with each tine element 86 inserted in the opposite end of the tine receiving cavity 84. To provide a bioabsorbable stent element in a substantially reduced configuration, the tine elements are inserted well into the tine receiving cavities as shown in FIG. 15. By suitably applying a expansion force to the interior of the reduced diameter stent, the tine elements 86 will slide relative to the bioabsorbable sheets 82 defining the tine receiving cavities 84 and thus enlarge the internal diameter of the stent as shown in FIG. 16. In accordance with this embodiment of the invention, the stent is retained in its reduced diameter configuration by the frictional interaction of the tine elements 86 and the tine receiving cavities 84. Likewise, in the enlarged configuration, frictional forces retain the tine elements 86 and tine receiving cavity portions 84 of the stent 80 in the desired orientation.

As schematically shown in FIG. 14, apertures 88 are defined both through the bioabsorbable sheets 82 defining the tine receiving cavities 84 and the tine elements 86 themselves so as to allow blood flow therethrough and/or endothelial tissue ingrowth. The bioabsorbable material itself which defines the tines and the tine receiving cavities can be porous to allow tissue ingrowth and/or to allow the incorporation of drugs therein as described more fully below. The apertures 88 schematically illustrated in FIG. 14 are for illustrative purposes only and the relative dimensions of the apertures 88 and the bioabsorbable material need not necessarily be as shown in that Figure.

Figure 17:
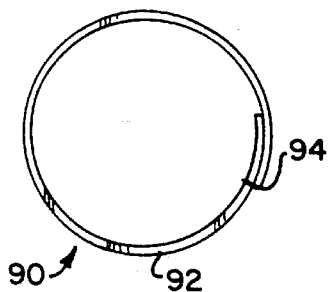
FIG. 17 is a perspective view of yet a further alternate embodiment of the invention.
Figure 18:
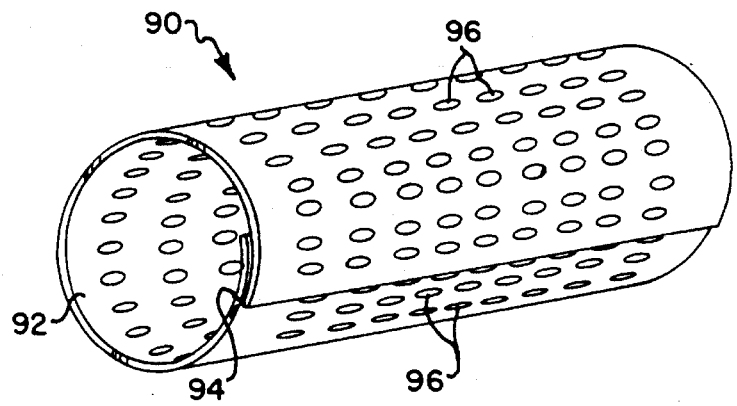
FIG. 18 is a schematic end view of the embodiment of FIG. 17.

In accordance with yet a further alternative embodiment of the invention as illustrated in particular in FIGS. 17 and 18, the stent 90 of the invention can be simply in the form of a rolled up sheet 92 of bioabsorbable material. Where the bioabsorbable material has shape retaining memory, the bioabsorbable material can be formed so as to be a roll of predetermined diameter which has been for example heat set. The stent is then forced, by further rolling the material, into a reduced diameter configuration which is maintained either by means of a buckle-like retention element 94 provided on the stent 90 itself or by capturing the stent 90 within or on a catheter element. When the force tending to maintain the stent in its reduced diameter configuration is released, then, the stent 90 will self expand to its original or close to its original diameter.

Where the stent is expandable, that is, one which retains substantially any shape into which it is distorted, the stent can be rolled into a reduced diameter configuration, which it retains naturally, and then, by applying an expanding force to the interior surface thereof, can be expanded to a desired diameter and will retain that substantially enlarged diameter upon the release of the expanding force.

As schematically illustrated in particular in FIG. 17, the bioabsorbable sheet 92 provided in accordance with this embodiment of the invention also has a plurality of pores and/or apertures 96 defined therethrough to allow blood flow through the stent 90 and/or tissue ingrowth for encapsulation. The bioabsorbable material can be porous and further can include apertures defined therethrough to enhance tissue encapsulation, bloodflow, therethrough and/or to provide cavities for receiving and carrying a drug to a targeted area of a body passage to be treated. In the alterative, as also detailed herein below, the material of the stent can have a drug incorporated therein when formed, which drugs will leach therefrom following placement in the body. The relative size of the apertures illustrated in particular in FIG. 17 is schematic and in actual practice, the pores or apertures through the stent may be larger or smaller then those illustrated.

As noted above, the stent formed in accordance with the present invention is preferably formed from a biodegradable polymeric material. The particular polymer selected and the thickness of the same, in particular, will determine the rates of biodegradation and bioabsorption and the structural characteristics of the stent during degradation and absorption should therefore be selected in accordance with the desired absorption period and characteristics of the stent.

Materials suitable for use in forming the bioabsorbable stents to which the invention relates are such that, when fabricated in the desired geometry, afford the stent sufficient strength to withstand collapse pressures of at least 100 mmHg, preferably at least 200 mmHg. Suitable materials do not produce toxic reactions, or act as carcinogens at the exposure levels present at the stent site. Suitable materials degrade and are absorbed with the production of physiologically acceptable breakdown products and the loss of strength and mass are appropriate to the particular biological environment and clinical function requirements.

In accordance with a preferred embodiment of the invention, the stent is formed of poly-L-lactide. Alternative preferred stent forming materials include copolymers of L-lactide with DL-lactide or D-lactide or glycolide, as well as homopolymers of beta-hydroxybutyric acid and its copolymers with other beta-hydroxy aliphatic acids. Polymers of omega hydroxy acids of the form $HO(CH_2)_nCO_2H$ where n is, preferably, 5–13 and polymers of aliphatic diacids and diols of the form $HO_2C-(CH_2)_x-CO_2H$ and $HO-(CH_2)_y-OH$, where x is, preferably, 4–16 and y is, preferably, 2–18, can also be used to make stents characterized by varying rates of hydrolytic degradation.

Polyamides of the form $-NH-(CH_2)_n-CO-$ and $NH-(CH_2)_x-NH-CO-(CH_2)_y-CO-$, where n is, preferably, 6–13 and where x is, preferably, 6–12 and y is, preferably, 4–16, can also be used particularly where degradation slower than that achieved with poly-L-lactide is advantageous.

Polyanhydrides from diacids of the form $HO_2C-C_6H_4-O-(CH_2)_nOC_6H_4-CO_2H$, where n is, preferably, 2–8, give a range of values of Young's modulus and absorption rates, and copolymers of these with, for example, aliphatic alpha-omega diacids of up to about 12 carbon atoms can be used to provide stents having accelerated bioabsorption rates, advantageous in certain circumstances.

Polyorthoesters, such as are formed by the reaction of $(RO)_3C-X-C(OR)_3$ with $(HOCH_2)_2CH-Y-CH(CH_2OH)_2$, where R is an alkyl group, preferably a lower alkyl such as $CH_3-$ or $C_2H_5-$, X and Y are, for example, $-C_6H_4-$ or $-(CH_2)_n-$ where n is 1–12, or combinations of $-C_6H_4-$ and $-CH_2-$ groups, can also be used. Such polyorthoesters degrade in a biological environment to yield products that are bioabsorbed. One skilled in the art will appreciate that by varying R, X and Y, a range of hydrophobic character and Youngs modulus can be achieved thus providing stents of varying stiffness and biodegradability.

As indicated above, polylactide is a preferred material for stent formation. The hydrolysis of polyesters such as the polylactides is catalyzed by both acid and base. The pH of blood (7.3–7.4) is not sufficient to catalyze the hydrolysis. However, any hydrolysis taking place in the interior of the polymer will produce acidic breakdown products (lactic acid and its oligomers) that slowly diffuse and act as catalysts to autoaccelerate the degradation. The rate of degradation can be further accelerated, where desirable, by adding excipients such as citric acid or fumaric acid, or other relatively nontoxic acids during the polymer processing. The addition of acids is, preferably, carried out after the last heating during the polymer processing to minimize degradation of the polymers prior to implantation. For example, fumaric acid can be incorporated into a solution of poly-L-lactide (for example, a methylene chloride solution) prior to dry spinning. The solvent can be readily evaporated, for example, in warm air, and the fibers fabricated into stents and set in shape. A loading of 0.1–1.0% fumaric acid in the polymer is preferred. Shelf life of stents with acid excipients can be extended by keeping them dry and away from high temperatures.

Exposure to gamma radiation can also be used to effect chain scission with resulting formation of acid groups which accelerate stent degradation. The higher the dose, the more quickly the stent will degrade.

Other additives that can be used to accelerate stent degradation and thus absorption are substances that are not themselves an acid but which hydrolyze to produce an acid more rapidly than the polymer. An example is the tert. butyl ester of an acid, such as lauric acid or ditert. butyl fumarate. Such additives break down in warm, wet acidic environments, so that once in vivo degradation is initiated, catalysts are generated that further accelerate degradation.

The same principles used to design additives that accelerate degradation of the polymer in vivo can also be used to make comonomers for use with lactide which accelerate degradation. For example, a low molecular weight polymer of tartaric acid can be made by treating tartaric acid with ethyl ortho acetate, evaporating off ethyl alcohol and ethyl acetate. This low molecular weight polyester which can contain a few ortho ester units can be incorporated into lactide and subjected to polymerizing conditions to give a lactide/tartrate copolymer with hydrolyzable groups which produce carboxylic acids. One skilled in the art will appreciate that there are a large number of such possible comonomers as well as polymer additives. Preferred are those that do not produce significant inflammatory or toxic reactions when used in vivo and those that give desired reproducible rates of degradation and absorption when used in vivo.

Comonomers or additives that give a buffering effect upon hydrolysis can be used to retard biodegradation when a slower degrading material is desired. For example, a small amount (about 1–5%) of alanine copolymerized with lactide can be used to retard biodegradation. Other amino acids can be incorporated via copolymerization to give segments such as $-NH-(CH_2)_n-CO-$ where n=1–17, preferably, 1 and 5–10, in order to retard degradation.

The non-limiting Example that follows describes the use of melt spinning in the stent preparation process. One skilled in the art will appreciate that melt spinning lowers the molecular weight. That is, the molecular weight achieved during polymerization is reduced, fairly rapidly, when the polymer is melted. Higher molecular weight in the final product can be advantageous in that it gives: i) increased strength and toughness; ii) improved elastic recovery after deformation; and iii) a reduced rate of degradation and absorption.

Spinning from solution can be used in lieu of high temperature (about 190° C.) melt extrusion. Methylene chloride (b.p. 55° C.) is a preferred solvent for use in such a process. The solvent can be removed during the spinning process by: i) evaporating solvent from the protofibers descending from a spinneret with warm air (known in the art as dry spinning), or ii) squirting the polymer solution into a liquid bath, the liquid being a non-solvent for the polymer but miscible with the solvent in the spinning solution, e.g. methyl alcohol (known in the art as wet spinning).

The stents to which the invention relates can have incorporated therein, or coated thereon, one or more drugs, such as smooth muscle cell inhibitors (for example, growth factor inhibitors or cytotonic agents) collagen inhibitors, vasodilators (for example, prostaglandins or analogs thereof), or anti-platelet and/or anti-thrombotic substances (for example, aspirin, heparin or tissue plasminogen activator). (Imaging agents, such as radio-opaque fillers can also be used, as can agents that improve streamlined blood flow, such as hydrogels.) Such stents are excellent drug delivery vehicles as they can be used to achieve high local drug concentrations directly at the area at risk, for example, for restenosis, while at the same time avoiding problems associated with systemic drug administration, for example, toxicity. Timed release of the drug from the stent can be achieved either by forming the stent so that slow diffusion from the stent-forming polymer itself is effected or by coating the stent in a manner such that slow diffusion of the drug through, or from, the coating is effected.

In a preferred embodiment, the outer portion of the stent (the "skin") is made porous after the stent has been fabricated to accommodate the drug. The pores can be filled with a drug/gel forming matrix by alternating vacuum and hydrostatic pressure (for example, up to 6,000–20,000 psi). If necessary, the stent can then be contacted with a reagent that causes the matrix to set as a gel.

The porous skin can be formed by dipping the stent, or filaments from which the stent is to be formed, into a solvent that swells the outer layer of the filaments. Ideally, diffusion of the solvent is effected fairly slowly; diffusion can be slowed, for example, by chilling the solvent. In this way the core of the filament is not affected during the time of exposure to solvent. The filament with swollen outer layer can then be dipped into an agent that is a "nonsolvent" for the polymer of which the filaments are made, which agent forms a solution with the swelling solvent. This agent, preferably, diffuses more rapidly than the first solvent. Warming can be used to promote diffusion of the agent into the swollen area thus causing phase separation that results in the formation of a porous skin on the stent filament. If poly-L-lactide is used as the polymer, chloroform can be used as the swelling solvent and methyl alcohol as the agent that causes phase separation. Pore formation can also be effected in polylactic/glycolic acid polymers and copolymers using a blend of, for example, orthoesters (such as a methyl or ethyl orthoformate or orthoacetate) and methylene chloride as solvent and water as nonsolvent. The change in CED of the orthoester/water reaction product can be expected to produce phase separation and the molecular weight of the orthoester will produce a low rate of diffusion out of the solvent. If nylon 6/6 is used as the polymer, 75% aqueous formic acid can be used as the swelling solvent and 5% aqueous formic acid as the phase separation agent. Other suitable polymer/solvent/agent combinations can also be used. One skilled in the art can readily determine appropriate solvents/agents to be used with any particular polymer.

An example of a suitable gelling system includes a mixture of sodium alginate and neutral heparin. After this is introduced into the pores, the filaments can be dipped in aqueous calcium chloride which causes the alginate to gel.

As indicated above drugs to be delivered can be incorporated into the stent. The manner in which the drug is incorporated depends on the spinning technology used (melt spinning, dry spinning or wet spinning). (See, generally, Rodriquiz.)

One skilled in the art will appreciate that, as melt spinning involves the heating of the polymer above its melting point, the range of drugs that can be used in conjunction with this method is somewhat limited. Drugs that are sufficiently stable and unreactive at the high temperatures involved can, however, be blended with the polymer prior to extrusion.

In dry spinning, the polymer is dissolved in a solvent and the solution is extruded, the solvent being removed by warm air. The same analysis applies as in melt spinning but the temperatures can be substantially lower, increasing the number of drugs that can be incorporated.

In wet spinning, the polymer is dissolved in a solvent and extruded into a second liquid that is a "nonsolvent" for the polymer but which will extract the solvent for the polymer and coagulate the fibers. The analysis for this process is the same as for the development of porous skin discussed above with respect to the relative diffussivities of the two liquids, but wet spinning gives pores throughout the fiber diameter. Drug can be incorporated by running the fibers through a bath post-congulation, and rinsing. The pores can then be partially collapsed by stretching, heating, or solvent exposure thereby trapping the drug throughout the filament. If a heat sensitive drug is incorporated, then subsequent processing steps used must avoid high temperature, e.g., the heat setting step can be replaced by chemical setting (see below).

Other methods can also be used to incorporate drugs into the stents of the present invention. For example, small water soluble particulates can be added to the polymer before extrusion and leached out post-fabrication to create pores. Monomeric lactide can be incorporated before extrusion and subsequently leached out. Very small pores can be created by swelling the polymer at any stage post-extrusion in a supercritical fluid such as propane and then reducing the pressure so that no liquid phase exists. In all cases, drug containing solutions can be forced into the pores by hydrostatic pressure with or without a gelling agent to control out-diffusion of the drug.

One skilled in the art will appreciate from the foregoing that the stent to which the invention relates can be used as a vehicle for delivering virtually any drug. Care must be taken, however, to ensure that the fabrication process, particularly in those situations where the drug is to be incorporated into the stent, is selected such that the activity of the drug to be delivered is not diminished or destroyed. In addition to use of the spinning technologies noted above, the temperature of the setting step of stent formation must also be considered. As an alternative to annealing, which involves heating to temperatures in the range of 110°–140° C., chemical setting can be used. Specifically, the stent can be exposed to vapors or liquid of a poor solvent or weak swelling agent such as ethyl acetate, then air or vacuum drying to remove the solvent/agent (0°–40° C.).

Drugs particularly sensitive to thermal deactivation (for example, proteins, including tissue plasminogen activator) are preferably incorporated into a porous skin formed on the stent, as described above. Sterilization of the stent in the case of such drugs can be effected using gamma radiation.

One skilled in the art will recognize that the amount of drug to be incorporated into, or coated on, the stent will depend on the therapy sought. Such determinations can be made without undue experimentation.

From a reading of the following non-limiting Example, one skilled in the art will appreciate that variations in molecular weights, dimensions, draw ratios, temperatures and solvents are all possible without substantially altering the product stent.

EXAMPLE

Stent Preparation

Rectangular or cylindrical monofilaments made by melt extrusion of poly-L-lactide with an average weight of 35,000 daltons were drawn to 600% of their original length to give a final diameter for the cylindrical filaments of 0.18 mm. These fibers were braided onto a 4- to 8-foot Teflon mandrel, 3.17 mm in diameter, using 8 ends in the braiding process (four filaments moving in clockwise and four in counterclockwise helices, each filament alternately going over and under the intersecting filaments). The filaments were then secured to the mandrel with two wire twists at intervals such that each interval was slightly longer than the desired stent (typically, 0.5–2.0 cm in length). The spacing of the two wire twists was such that after annealing the mandrel and fiber could be cut between the wires to give a single stent length while constraining the fibers form shrinking during annealing. (The purpose of annealing is to heat set the fibers so they will return to a helical form if distorted after annealing.) The annealing was carried out at 140° C. for 15 minutes. (Higher temperatures (below the melting point) allow shorter annealing cycles and lower temperatures down to about 110° work better with longer times.) The annealing was done in air although an inert atmosphere such as nitrogen or vacuum annealing result in somewhat higher molecular weight products.

The filaments of the partially formed stents were glued together at the desired terminal intersections, thereby determining the final length, with a small drop of a solution of poly-L-lactide in a volatile solvent such as chloroform, and removed from the mandrel. When the solvent has substantially evaporated, the stents are trimmed to remove most of the fibers beyond the glue joints and each joint is brought into proximity with a hot wire causing the ends to fuse and become smooth.

While the invention has been described in connection with what is presently considered to be the most practical and preferred embodiment, it is to be understood that the invention is not to be limited to the disclosed embodiment, but, on the contrary, is intended to cover various modifications and equivalent arrangement included within the spirit and scope of the appended claims. For example the preformed stent need not be a right cylinder but could have a cross-section which varies along the length of the stent. Further, solvent setting can be used in lieu of thermal annealing. Solvent setting is particularly advantageous where drugs are to be incorporated into the stent. In addition, the self expanding stent of the invention could advantageously be used in body passages other than the coronary arteries, such as the ureters or the fallopian tubes, such alternative applications and configurations being limited only by the appended claims.

What is claimed is:

1. A method of forming pores on the surface of a stent, the stent including a tubular main body portion having a first end, a second end, and a flow passage defined therethrough from said first end to said second end, said tubular main body portion being sized for intraluminal placement within a body passage, said main body portion being one of porous and apertured, at least in part, said main body portion being one of expandable and self-expanding from a first, reduced cross-sectional dimension to a second enlarged cross-sectional dimension whereby said main body portion can be transported intraluminally to a targeted portion of a body passage and expanded to a second enlarged diameter so as to engage and support said targeted portion of said body passage, the method comprising the steps of:
   i) contacting material from which said stent is formed with a solvent that swells said material under conditions such that swelling of an outer layer of said material is effected; and
   ii) contacting said material resulting from step (i) with an agent that is a nonsolvent for said material, which agent forms a solution with said solvent, under conditions such that said agent diffuses into said swollen outer layer of said material thereby causing phase separation and pore formation in said outer layer of said material.

2. The method according to claim 1, wherein said pores are formed in said outer layer of said material prior to formation of said stent from said material.

3. The method according to claim 1, wherein said pores are formed in said outer layer of said material after formation of said stent from said material.

4. The method according to claim 1, wherein said main body portion is formed at least in part from a bioabsorbable material.

5. A method of incorporating a drug into a stent, the stent including a tubular main body portion having a first end, a second end, and a flow passage defined therethrough from said first end to said second end, said tubular main body portion being sized for intraluminal placement within a body passage, said main body portion being one of porous and apertured, at least in part, said main body portion being one of expandable and self-expanding from a first, reduced cross-sectional dimension to a second enlarged cross-sectional dimension whereby said main body portion can be transported intraluminally to a targeted portion of a body passage and expanded to a second enlarged diameter so as to engage and support said targeted portion of said body passage, said stent having a therapeutically effective amount of a drug coated thereon or incorporated therewithin, the method comprising the steps of:
   i) forming pores in an outer layer of material from which said stent is formed;
   ii) introducing into said pores a composition comprising said drug and a gel forming agent; and
   iii) effecting setting of said composition as a gel.

6. The method according to claim 5, wherein said main body portion is formed at least in part from a bioabsorbable material.

7. An intraluminal stent comprising a tubular main body portion having a first end, a second end, and a flow passage defined therethrough from said first end to said second end, said tubular main body portion being sized for intraluminal placement within a body passage, said main body portion being formed at least in part from a material which has been rolled into a substantially cylindrical configuration and thereby said main body portion has a central axis, said main body portion being one of porous and apertured with a plurality of apertures, at least in part, said main body portion being expandable from a first, reduced cross-sectional dimension to a second enlarged cross-sectional dimension whereby said main body portion can be transported intraluminally to a targeted portion of a body passage and then can be expanded to said second enlarged cross-sectional dimension so as to engage and support said targeted portion of said body passage, said main body portion including means for retaining said main body portion in said reduced cross-sectional configuration and means for retaining said main body portion in said enlarged cross-sectional configuration, said main body portion being in the form of at least one strip of material, said means for retaining comprising an elongated connector element provided adjacent a first end of said strip of material, said connector element having a radially inner wall and a radially outer wall defining therebetween a strip receiving passage extending in a first direction from a first open end to a second end thereof, said strip receiving passage extending in said first direction at least part circumferentially of said main body portion, said strip of material being slidably disposed in said strip receiving passage whereby sliding movement of said strip of material in said first direction decreases a diameter of said main body portion and sliding movement of said strip of material in a second direction, opposite to said first direction, increases a diameter of said main body portion, at least a portion of said strip of material being disposed in said passage when said main body portion has said first cross-sectional dimension and at least a portion of said strip of material being disposed in said passage when said main body portion has said second cross-sectional dimension, wherein said second end of said passage is open, and said strip of material extends through said passage to selectively protrude from said first and second open ends thereof.

8. A stent as in claim 7, wherein said means for retaining comprises frictional engagement between said strip of material and said connector element.

9. A stent as in claim 7, wherein first and second connector elements are provided, one of said connector elements being fixedly secured to said first end of said strip of material.

10. A stent as in claim 9, wherein each of said connector elements includes means for slidably receiving said strip of material.

11. A stent as in claim 7, wherein a plurality of strips of material are provided.

12. The stent according to claim 7, wherein said main body portion is formed at least in part from a bioabsorbable material.

13. The stent according to claim 7, wherein said main body portion has a therapeutically effective amount of a drug coated thereon or incorporated therewithin.

14. An intraluminal stent comprising a tubular main body portion having a first end, a second end, and a flow passage defined therethrough from said first end to said second end, said tubular main body portion being sized for intraluminal placement within a body passage, said main body portion being formed at least in part from a material which has been rolled into a substantially cylindrical configuration and thereby said main body portion has a central axis, said main body portion being one of porous and apertured, at least in part, said main body portion being expandable from a first, reduced cross-sectional dimension to a second enlarged cross-sectional dimension whereby said main body portion can be transported intraluminally to a targeted portion of a body passage and then can be expanded to a second enlarged diameter so as to engage and support said targeted portion of said body passage, said main body portion including means for retaining said main body portion in said reduced diameter configuration and means for retaining said main body portion in said enlarged diameter configuration, said main body portion including a plurality of tine receiving cavities and a plurality of tine elements, said tine receiving cavities each extending in a first direction at least part circumferentially of said main body portion from a first open end to a second end thereof, said tine elements being slidable in respective tine receiving cavities whereby sliding movement of said tine elements in said first direction in said tine receiving cavities selectively increases or decreases a diameter of said main body portion.

\* \* \* \* \*